United States Patent [19]

Kushibe et al.

[11] Patent Number: 5,672,482

[45] Date of Patent: Sep. 30, 1997

[54] METHOD FOR PURIFYING CYCLIC INULOOLIGOSACCHARIDE

[75] Inventors: Sachiko Kushibe; Masao Tamura, both of Tokyo, Japan

[73] Assignees: Mitsubishi Chemical Corporation; Mitsubishi Kasei Engineering Company, both of Tokyo, Japan

[21] Appl. No.: 418,770

[22] Filed: Apr. 7, 1995

[30] Foreign Application Priority Data

Apr. 15, 1994 [JP] Japan .................................. 6-077645

[51] Int. Cl.⁶ .......................... C12Q 1/48; C12Q 1/34; C12Q 1/02; C07H 1/06

[52] U.S. Cl. .................. 435/15; 435/18; 435/29; 435/74; 435/252.31; 435/4; 536/127; 536/124; 536/123.1; 536/4.1; 536/1.11

[58] Field of Search .............. 435/15, 74, 252.31, 435/29, 4, 18; 536/127, 124, 123.1, 4.1, 1.11

[56] References Cited

U.S. PATENT DOCUMENTS 4,613,377 9/1986 Yamazaki et al. ..................... 435/15

4,617,269 10/1986 Rathbone et al. ..................... 435/97
4,849,356 7/1989 Van Dooren et al. ................ 435/15
5,089,401 2/1992 Fujita et al. ........................... 435/97
5,089,402 2/1992 Uchiyama et al. .................... 435/96
5,122,460 6/1992 Uchiyama et al. .................... 435/96

FOREIGN PATENT DOCUMENTS

| 0279946 | 8/1988 | European Pat. Off. . |
| 0 440 074 | 8/1991 | European Pat. Off. . |
| 0 470 331 | 2/1992 | European Pat. Off. . |
| 63-51000 | 10/1988 | Japan . |
| 022550085 | 10/1990 | Japan . |
| 2-252701 | 10/1990 | Japan . |
| WO94/10295 | 11/1994 | WIPO . |

*Primary Examiner*—Louise Leary
*Attorney, Agent, or Firm*—Wenderoth, Lind & Ponack

[57] ABSTRACT

An exo-enzyme having an ability to cut $\beta$-(2→1) fructoside bond or a microorganism which produces the enzyme is allowed to act on a saccharide solution containing cyclic inulooligosaccharide in which fructose molecules are bonded through $\beta$-(2→1) bond in a cyclic configuration, and other saccharides such as monosaccharide, disaccharide, linear oligosaccharide and inulin, and then the cyclic inulooligosaccharide is collected from an obtained saccharide solution. Thus cyclic inulooligosaccharide can be purified inexpensively at a high yield without using any solvent.

6 Claims, No Drawings

METHOD FOR PURIFYING CYCLIC INULOOLIGOSACCHARIDE

TECHNICAL FIELD

The present invention relates to a method for efficiently separating and purifying objective cyclic inulooligosaccharide from saccharide solution including it by effecting an enzymatic treatment.

BACKGROUND ART

Cyclodextrin in which 6–8 glucoses are bonded is known as a cyclic oligosaccharide. Cyclodextrin is noted as a clathrate agent for food, and it contributes to the realization of high added values of food for purposes of maintenance of flavor components, masking of peculiar order, removal of bitterness, prevention of oxidation and so on. It is also utilized in various manners in fields other than food. However, cyclodextrin has a low solubility in water, and its industrial applicability is limited in the present circumstances.

Cyclic inulooligosaccharide is a saccharide in which fructose molecules are bonded through $\beta$-(2→1) bond in a cyclic configuration. It is a new substance, and its production was first reported in Japanese Patent Laid-open Nos. 2-252701 (October 1990) and 2-255085 (October, 1990), wherein an enzyme originating from *Bacillus circulans* MZ No. 31, that is cyclic inulooligosaccharide fructanotransferase (hereinafter abbreviated as "CFTase"), is allowed to act on inulin. The cyclic inulooligosaccharide is known to exist as cycloinulohexaose, cycloinuloheptaose, and cycloinulooctaose comprising six, seven and eight fructose residues, respectively. The cyclic inulooligosaccharide has an extremely high solubility in water, and it can be expected to be utilized in fields in which application of cyclodextrin is limited due to low solubility in water.

Cyclodextrin forms a bucket-shaped cylindrical structure in which a hydrophilic region is distinguished from a hydrophobic region. On the contrary, it is reported that the structure of cyclic inulooligosaccharide lies in a different stereostructure from that of cyclodextrin, wherein its intermolecular cavity is small, a crown ring having $\beta$-(2→1) fructoside bond portions is formed in its molecule, and configurations like 18-crown-6, 21-crown-7, and 24-crown-8 are respectively formed by cycloinulohexaose, cycloinulopentaose and cycloinulooctaose, having a ring like a crown ether therein (M. Sawada et al., *Carbohydr. Res.*, 217, 7–17 (1991), etc.). In addition, it has been also revealed that cyclic inulooligosaccharide has an ability to selectively capture metallic ions like a crown ether (N. Yoshie et al., *Chem. Lett.*, 353–356 (1993), Japanese Patent Laid-open No. 5-76756 (Mar. 30, 1993), etc.). The crown ether has a problem in safety, and also has a problem that it is extremely expensive. Accordingly, the cyclic inulooligosaccharide is noted as a new functional saccharide for which not only applications as those for cyclodextrin but also applications as those for crown ether can be expected. Cyclic inulooligosaccharide is produced by allowing CFTase to act on inulin. However, it is inevitable to involve by-products as contaminants other than cyclic inulooligosaccharide existing in a reaction solution, including, for example, unreacted inulin monosaccharides such as fructose and glucose, and linear oligosaccharides formed by some monosaccharides bonded linearly. Thus a step is required for separation and purification of cyclic inulooligosaccharide. A purification method based on chromatographic separation in an aqueous system using a gel resin has been hitherto utilized in separation and purification of saccharide. Such a method can remove low-molecular weight monosaccharides, disaccharides and/or unreacted inulin, however, linear oligosaccharides have been difficult to separate because their affinity to the resin is closely similar to that of cyclic inulooligosaccharide.

On the other hand, methods for separating and purifying cyclic inulooligosaccharide from a saccharide solution containing cyclic inulooligosaccharide have been hitherto known, such as a method for fractionation by using activated carbon (Japanese Patent Laid-open No. 2-252701 (Oct. 11, 1990)), and a method for fractionation by using a silica carrier comprising siloxane (1992 Annual Meeting of The Society for Fermentation and Bioengineering, Japan, WO94/10295 (Nov. 5, 1994), etc.). However, in any of these methods, cyclic inulooligosaccharide is eluted by using alcohol, and thus a continuous operation is difficult because of an operative problem that bubbles are generated when the solvent is changed from an aqueous system to an organic solvent system. Also, the effect has not been sufficient judging from a viewpoint of yield. Further, there are many problems such as the increase in purification cost due to the use of alcohol, the treatment of waste liquid and so on. Therefore, industrial production has been difficult in the present circumstances. Thus it has been desired to develop an efficient method for purifying cyclic inulooligosaccharide without using alcohol.

DISCLOSURE OF THE INVENTION

As a result of diligent studies by the present inventors in order to develop a method for efficiently purifying cyclic inulooligosaccharide from a saccharide solution comprising cyclic inulooligosaccharide, monosaccharide, disaccharide, linear oligosaccharide and inulin, it has been found that objective cyclic inulooligosaccharide can be efficiently selected and separated by converting contaminants other than cyclic inulooligosaccharide existing in such a saccharide solution, such as disaccharide, linear oligosaccharide and unreacted inurin, into low-molecular weight molecules by using a hydrolase, and the present invention has been completed.

Namely, the gist of the present invention lies in a method for purifying cyclic inulooligosaccharide, wherein an exoenzyme having an ability to cut $\beta$-(2→1) fructoside bond or a microorganism which produces the enzyme is allowed to act on a saccharide solution containing cyclic inulooligosaccharide in which fructose molecules are bonded through $\beta$-(2→1) bond in a cyclic configuration, and at least one of saccharides selected from disaccharide, linear oligosaccharide and inulin, and then the cyclic inulooligosaccharide is collected from an obtained saccharide solution.

The present invention will now be explained in detail below.

The cyclic oligosaccharide which can be purified according to the present invention includes cyclic inulooligosaccharides in which fructose molecules are bonded through $\beta$-(2→1) bond in a cyclic configuration, such as cycloinulohexaose (six fructose molecules are bonded through $\beta$-(2→1) bond in a cyclic configuration), cycloinuloheptaose (seven fructose molecules are bonded through $\beta$-(2→1) bond in a cyclic configuration), and cycloinulooctaose (eight fructose molecules are bonded through $\beta$-(2→1) bond in a cyclic configuration).

The linear oligosaccharide as defined in the present invention are those in which three to several tens of saccharide members are bonded, including, for example, fructooligosaccharides and inulooligosaccharides in which the reducing end is glucose and two to several tens of fructoses are bonded, and fructose polymers in which three to several tens of fructoses are bonded. The disaccharide includes, for example, sucrose and inulobiose. The monosaccharide includes, for example, fructose and glucose.

The saccharide solution containing cyclic inulooligosaccharide and other saccharides such as monosaccharide, disaccharide, linear oligosaccharide and inulin (hereinafter abbreviated as "cyclic inulooligosaccharide-containing saccharide solution") can be obtained by the action of CFTase or a microorganism which produces CFTase such as *Bacillus circulans* MZ No. 31 (FERM P-9943) and *Bacillus circulans* MCI-2554 (FERM P-11940), in an extract solution of a plant having a high inulin content such as *Helianthus tuberosus* L., *Arctium lappa* L. and *Cichorium intybus* L. and/or a solution containing inulin as a carbon source. In this context, microbial cells of the microorganism themselves may be allowed to act. Alternatively, CFTase is extracted from the microbial cells, and the action may be conducted by using it exactly as it is or after purification, immobilization and so on. Alternatively, recombinant CFTase produced by gene engineering may be used as the CFTase. In this aspect, the recombinant CFTase may be used for the reaction in the same method as the natural CFTase, or a transformant which produces the recombinant CFTase may be used for the reaction.

The cyclic inulooligosaccharide-containing saccharide solution may be obtained by cultivating a microbial strain as described above in an extract solution of the aforementioned plant having a high inulin content and/or a culture medium containing inulin as a carbon source, and processing a culture supernatant thereof. In this case, the culture medium has a composition containing, for example, 1–40% inulin as a carbon source, and containing soybean powder, wheat germ, corn steep liquor, cotton seed oil, meat extract, peptone, yeast extract, ammonium sulfate, sodium nitrate, urea and so on as a nitrogen source. The microorganism for production is inoculated in the culture medium optionally further added with inorganic salts or the like for providing ions of sodium, potassium, calcium, magnesium, cobalt, chlorine, phosphate, sulfate and so on, and cultivation is performed with shaking. Herein the cultivation temperature is 20°–40° C. With respect to the cultivation period, the cultivation may be performed for a period of time optimum for the microorganism to be used, namely for a period of time optimum for production of CFTase and production of cyclic inulooligosaccharide in a culture supernatant thereof. Microbial cells are removed from an obtained culture liquid by centrifugation or the like, and a solution obtained by inactivating the enzyme in a supernatant thereof is provided as the cyclic inulooligosaccharide-containing saccharide solution.

In the case of the action of the enzyme of CFTase itself, for example, microbial cells are removed from the culture liquid after the cultivation in accordance with the method as described above by means of centrifugation or the like, and an obtained culture supernatant may be used to make the action. Alternatively, the supernatant may be further purified, and partially purified enzyme or purified enzyme may be used to make the action. In the case of the action using the culture supernatant, partially purified enzyme or purified enzyme, for example, a cyclic inulooligosaccharide-containing saccharide solution is obtained by the action for 30 minutes or more at a temperature of 30°–70° C. in a 0.01–0.3M phosphate buffer adjusted to pH 7.0 containing about 0.5% or more of inulin.

The exo-enzyme having an ability to cut $\beta$-(2→1) fructoside bond (hereinafter abbreviated as "oligosaccharide cutting enzyme") or the microorganism which produces the enzyme is allowed to act on the cyclic inulooligosaccharide-containing saccharide solution, and components other than cyclic inulooligosaccharide and monosaccharide in the cyclic inulooligosaccharide-containing saccharide solution, specifically fructans such as disaccharide, linear oligosaccharide and unreacted inulin are converted into low-molecular weight molecules. Preferably, fructans such as disaccharide, linear oligosaccharide and inulin are enzymatically decomposed into monosaccharide and/or disaccharide, and they are removed. Thus purified cyclic inulooligosaccharide is obtained.

The oligosaccharide cutting enzyme is not specifically limited provided that it is an exo-enzyme which acts on fructans such as disaccharide, linear oligosaccharide and inulin, cuts their $\beta$-(2→1) fructoside bond, and decomposes them into monosaccharide and/or disaccharide. Specifically, there may be exemplified $\beta$-fructofuranosidase (called invertase or saccharase, as well), inulinase, and inulobiose generating enzyme. Any of these enzymes has no problem for their origin, and may be those commercially available. Microbial cells which produce these enzymes, or enzymes secreted outside the microbial cells may be used to make the action as they are. Alternatively, microbial cells or enzymes secreted outside the microbial cells may be purified and used to make the action.

As the microorganism which produces $\beta$-fructofuranosidase, there are known microorganisms belonging to the genera Saccharomyces, Candida, Bacillus, Fusarium, Neurospora, Aspergillus, Zymomonas and so on (*The Enzymes* (3rd ed.), 5, 291–305 (1971), etc.). As the microorganism which produces inulinase, there are known microorganisms belonging to the genera Aspergillus, Penicillium and so on (Japanese Patent Laid-open Nos. 62-208277 (Sep. 12, 1987), 62-228293 (Oct. 7, 1987), 3-83581 (Apr. 9, 1991), 3-198774 (Aug. 29, 1991), 4-190789 (Jul. 9, 1992), etc.). As the microorganism which produces inulobiose generating enzyme, there are known microorganisms belonging to the genus Arthrobactor and so on (T. Uchiyama et al., *Denpun Kagaku*, 35, 113–120 (1988), etc.).

A method for making the action of the oligosaccharide cutting enzyme or the microorganism which produces the enzyme on the cyclic inulooligosaccharide-containing saccharide solution is as follows. The oligosaccharide cutting enzyme, the microorganism which produces the enzyme, a culture supernatant of the microorganism which produces the enzyme, or immobilized enzyme or immobilized microbial cells obtained by immobilizing the above to a suitable carrier may be allowed to act at 30°–70° C. for 30 minutes or more on a cyclic inulooligosaccharide-containing saccharide solution at a concentration of about 5–70 in Brix scale in a 0.01–0.3 M phosphate buffer adjusted to about pH 4.5–8.5. Thus fructans such as disaccharide, linear oligosaccharide and inulin in the cyclic inulooligosaccharide-containing saccharide solution can be converted into low-molecular weight molecules.

The objective cyclic inulooligosaccharide can be separated and purified by using a known means from such a cyclic inulooligosaccharide-containing saccharide solution after the enzyme treatment. The cyclic inulooligosaccharide can be efficiently separated from monosaccharide and/or disaccharide by contacting the obtained inulooligosaccharide-containing saccharide solution after the enzyme treatment with a suitable gel-type filtration material. A gel cation exchanger is preferably used as the gel-type filtration material in this case. Especially a gel cation exchanger having a degree of crosslinking of 4–8% of an alkaline metal or alkaline earth metal form is preferably used. Such a cation exchanger is specifically exemplified by ion exchange resins such as DIAION® UBK-530, DIAION® UBK-535, DIAION® UBK-550, and DIAION® UBK-555 (each of which is produced by Mitsubishi Chemical Corporation).

A concrete purification method is as follows. At first, the aforementioned gel filtration material is made into slurry with deionized water, and packed to a separation column after air bubbles are sufficiently removed. The cyclic inulooligosaccharide-containing saccharide solution after the enzyme treatment is fed to the column in an amount of ½–¹/₁₀₀, preferably ⅕–¹/₂₀ of a volume of the charged filtration material. The eluant of water is followed to fractionate feed stock into a cyclic inulooligosaccharide fraction and other fractions. The cyclic inulooligosaccharide fraction is decolorized and deionized, and then concentrated and dried to a solid. Thus desired inulooligosaccharide can be obtained.

In order to improve the separation efficiency and reduce the amount of elute to be used, various known chromatographic separation techniques and a simulated moving-bed method may be used. Thus more effective fractionation can be performed.

BEST MODE FOR CARRYING OUT THE INVENTION

The present invention will be more specifically explained below with reference to Examples. However, the present invention is not limited to the following Examples, as far as one does not deviate from the gist of the present invention.

<EXAMPLE 1>

A medium (150 ml) containing 5% inulin, 0.2% yeast extract, 0.5% sodium nitrate, 0.05% magnesium sulfate, 0.05% potassium chloride, 0.05% potassium primary phosphate, and 0.001% ferric chloride was adjusted to pH 7.0, and sterilized with steam at 120° C. for 20 minutes. The sterilized medium was inoculated with a microorganism of *Bacillus circulans* MCI-2554 once with a platinum loop, and cultivated with shaking at 160 rpm at 30° C. for 35 hours. After completion of the cultivation, microbial cells were removed by centrifugation, and a culture filtrate was obtained. The obtained culture supernatant (100 ml) was used as a cyclic inulooligosaccharide-containing saccharide solution to conduct the following operation.

Invertase (3 mg, produced by Sigma) was added to the cyclic inulooligosaccharide-containing saccharide solution, and allowed to act at 50° C. for 6 hours. Invertase was inactivated by heating it at 100° C. for 10 minutes, and denatured protein was removed by centrifugation. An obtained reaction solution was analyzed by high speed liquid chromatography. As a result, cyclic inulooligosaccharide, fructose, glucose and sucrose in an extremely minute amount were merely found as saccharide contents.

The reaction solution was concentrated to give a Brix scale of 50, and used as a feed stock for column chromatography. Namely, an ion exchange resin (160 ml, DIAION® UBK-550, produced by Mitsubishi Chemical Corporation) was charged to a column having an inner diameter of 17 mm and a length of 700 mm, and water was allowed to flow to stabilize the column bed. Thereafter the aforementioned concentrated solution (8 ml) was fed, and then water was fed at a flow rate of 100 ml/h to conduct fractionation into fractions enriched by cyclic inulooligosaccharide and other fractions. The fractions containing cyclic inulooligosaccharide were collected, desalted and decolorized, followed by analysis with high speed liquid chromatography. As a result, objective cyclic inulooligosaccharide was obtained with a recovery of 91%.

<EXAMPLE 2>

A medium (150 ml) containing 1% inulin, 0.2% yeast extract, 0.5% sodium nitrate, 0.05% magnesium sulfate, 0.05% potassium chloride, 0.05% potassium primary phosphate, and 0.001% ferric chloride was adjusted to pH 7.0, and sterilized with steam at 120° C. for 20 minutes. The sterilized medium was inoculated with a microorganism of *Bacillus circulans* MCI-2554 once with a platinum loop, and cultivated with shaking at 160 rpm at 30° C. for 35 hours. After completion of the cultivation, microbial cells were removed by centrifugation, and a culture filtrate was obtained. The obtained culture supernatant (100 ml) was used as a crude enzyme solution. This was added with inulin to give a final concentration of 10%, and reacted at 37° C. for 15 hours. An obtained reaction solution was used as a cyclic inulooligosaccharide-containing saccharide solution to conduct the following operation.

Invertase (3 mg, produced by Sigma) was added to the cyclic inulooligosaccharide-containing saccharide solution, and allowed to act at 50° C. for 6 hours. Invertase was inactivated by heating it at 100° C. for 10 minutes, and then denatured protein was removed by centrifugation. An obtained reaction solution was analyzed by high speed liquid chromatography. As a result, cyclic inulooligosaccharide, fructose, glucose and sucrose in an extremely minute amount were merely found as saccharide contents.

The reaction solution was concentrated to give a Brix scale of 50, and used as a feed stock for column chromatography. Namely, an ion exchange resin (160 ml, DIAION® UBK-530, produced by Mitsubishi Chemical Corporation) was charged to a column having an inner diameter of 17 mm and a length of 700 mm, and water was allowed to flow to stabilize the column bed. Thereafter the aforementioned concentrated solution (8 ml) was fed, and then water was fed at a flow rate of 100 ml/h to conduct fractionation into fractions enriched by cyclic inulooligosaccharide and other fractions. The fractions containing cyclic inulooligosaccharide were collected, desalted and decolorized, followed by analysis with high speed liquid chromatography. As a result, objective cyclic inulooligosaccharide was obtained with a recovery of 94%.

<EXAMPLE 3>

A reaction solution after the treatment with invertase of a cyclic inulooligosaccharide-containing saccharide solution obtained in the same manner as Example 2 was concentrated to Give a Brix scale of 50, and used as a feed stock for column chromatography. Namely, four columns having an inner diameter of 28 mm and a height of 500 mm, in which an ion exchange resin (310 ml, DIAION® UBK-530, produced by Mitsubishi Chemical Corporation) was packed, were connected in series. The concentrated solution was supplied to one end of the columns at a flow rate of 600 ml/h for 10 minutes in a state of a column temperature maintained at 60° C., thereafter water was fed at a flow rate of 600 ml/h and allowed to flow out from the other end while developing and separating the concentrated solution in the columns. Objective cyclic inulooligosaccharide began to flow out at 42 minutes after the feeding of water, and thus collection was started to obtain cyclic inulooligosaccharide-containing fractions. Elution of cyclic inulooligosaccharide was approximately completed at 64 minutes thereafter, and elution of disaccharide began. Thus collection of samples was stopped.

The fractions containing cyclic inulooligosaccharide were collected, desalted and decolorized, followed by analysis with high speed liquid chromatography. As a result, the recovery of cyclic inulooligosaccharide was 94%.

<EXAMPLE 4>

A crude enzyme solution (100 ml) was obtained from a culture liquid of a microorganism of Bacillus circulans MCI-2554 in the same manner as Example 2.

An ion exchange resin (5 g, DIAION® WA30, produced by Mitsubishi Chemical Corporation) was added as a carrier for immobilization to the crude enzyme solution, and shaken for 2 hours at 30° C. to allow the carrier to absorb the enzyme to immobilize the enzyme. The immobilized enzyme was charged to a column, and washed with water. Thereafter a 5% inulin solution was allowed to flow at a space velocity of 0.2 to make the action. An obtained reaction solution was used as a cyclic inulooligosaccharide-containing saccharide solution to conduct the following operation.

Invertase (1 mg, produced by Sigma) was added to the cyclic inulooligosaccharide-containing saccharide solution (100 ml), and allowed to act at 50° C. for 6 hours. The enzyme was inactivated by heating it at 100° C. for 10 minutes, and denatured protein was removed by centrifugation. An obtained reaction solution was analyzed by high speed liquid chromatography. As a result, cyclic inulooligosaccharide, fructose, glucose and sucrose in an extremely minute amount were merely found as saccharide contents.

The reaction solution was concentrated after desalting and decolorizing to give a Brix scale of 50, and used as a material for column chromatography. An ion exchange resin (160 ml, DIAION® UBK-530, produced by Mitsubishi Chemical Corporation) was packed to a column having an inner diameter of 17 mm and a length of 700 mm, and water was allowed to flow to stabilize the column bed. Thereafter the aforementioned concentrated solution (8 ml) was fed, and then water was fed at a flow rate of 100 ml/h to conduct fractionation into fractions enriched by cyclic inulooligosaccharide and other fractions. The fractions containing cyclic inulooligosaccharide were collected, desalted and decolorized, followed by analysis with high speed liquid chromatography. As a result, the recovery of cyclic inulooligosaccharide was 90%.

<EXAMPLE 5>

A cyclic inulooligosaccharide-containing saccharide solution obtained in the same manner as Example 2 was reacted with immobilized invertase.

Ground and dried microbial cells of yeast (5 g, produced by Sigma), 25% glutaraldehyde (4 ml), 3% polyethyleneimine solution (4 ml), and water (100 ml) were added and mixed. Microbial cells were precipitated from the mixture by centrifugation (5000 rpm, 5 minutes), washed twice with water, and precipitated by centrifugation at 13000 rpm for 15 minutes. The precipitate was molded by extrusion with a syringe, and dried under a nitrogen flow to provide immobilized invertase.

The immobilized invertase (7.56 g) was reacted with the cyclic inulooligosaccharide-containing saccharide solution (100 ml) at 50° C. for 5 hours. An obtained solution was heated at 100° C. for 10 minutes to inactivate the enzyme, and denatured protein was removed by centrifugation. An obtained reaction solution was fractionated by using an ion exchange resin in the same manner as the method described in Example 2, followed by analysis with high speed liquid chromatography. As a result, the recovery of cyclic inulooligosaccharide was 92%.

<EXAMPLE 6>

A cyclic inulooligosaccharide-containing saccharide solution was reacted with immobilized invertase in the same manner as Example 5. An obtained reaction solution was concentrated to give a Brix scale of 60, and then used as a feed stock for column chromatography.

A chromatographic separation system described in Japanese Patent Laid-open No. 63-158105 (Jul. 1, 1988) was adopted, in which the upstream end of a bed packed with the adsorbent is connected to its downstream end by a fluid channel to enable the fluid to flow circulatively from the upstream end of the packed bed to its downstream end. An ion exchange resin (DIAION® UBK-530, produced by Mitsubishi Chemical Corporation) was used as a adsorbent, and water was used as a eluant agent. The adsorbent was packed in a total amount of 1240 ml to four columns having an inner diameter of 28 mm and a length of 500 mm connected in series. The charged bed was maintained at 65° C. Both the volume flow rate of feed stock and eluant are 600 ml/h. The first column was used solely for supply, and the fourth column was used solely for withdrawal. The separating operation was performed until a stable state was achieved in accordance with a time schedule shown in the following Table 1. Compositions of components of each of fractions after achievement of a stable state are shown in the following Table 2.

TABLE 1

| Step | Supplied fluid | Withdrawn fluid | Time |
|---|---|---|---|
| 1 | raw material | monosaccharide/ disaccharide fraction | 20 minutes |
| 2 | water | monosaccharide/ disaccharide fraction | 15 minutes |
| 3 | water | cyclic inulo- oligosaccharide fraction | 35 minutes |
| 4 | (circulation) | (circulation) | 10 minutes |

TABLE 2

| Component | Raw material | Cyclic inulo- oligosaccharide fraction | Monosaccharide/ disaccharide fraction |
|---|---|---|---|
| Cyclic inulo- oligosaccharide | 50.2 | 99.2 | 0.7 |
| Disaccharide | 0.3 | 0.4 | 0.1 |
| Monosaccharide | 49.5 | 0.4 | 99.2 |

(unit: % by weight)

<EXAMPLE 7>

A cyclic inulooligosaccharide-containing saccharide solution obtained in the same manner as Example 2 was enzymatically treated with invertase. An obtained reaction solution was concentrated to Give a Brix scale of 52, and separation was performed by means of a simulated moving-bed method (Japanese Patent Laid-open No. 2-49159 (Feb. 19, 1990). An ion exchange resin (DIAION® UBK-530, produced by Mitsubishi Chemical Corporation) was used as an adsorbent agent, on condition that the amount of the adsorbent agent was 1288 ml, the operation temperature was 60° C., the operation load was 0.0617 (l/h), and the elute flow rate ratio was 3.3 (v/v). The resulting average flow amount of cyclic inulooligosaccharide was 140.9 ml/h. Obtained cyclic inulooligosaccharide was collected, desalted and decolorized, followed by analysis with high speed liquid chromatography. As a result, the recovery of cyclic inulooligosaccharide was 97%.

Industrial Applicability

According to the purification method of the present invention, objective cyclic inulooligosaccharide can be purified inexpensively at a high yield without using any solvent from a solution containing cyclic inulooligosaccharide. It is expected for obtained cyclic inulooligosaccharide to be utilized in a field of chemicals as well as other various fields.

What is claimed is:

1. A method for purifying cyclic inulooligosaccharide, comprising the steps of:

allowing an exo-enzyme having an ability to cut β-(2→1) fructoside bond or a microorganism which produces the exo-enzyme to act on a saccharide solution containing (a) cyclic inulooligosaccharide in which fructose molecules are bonded through β-(2→1) bond in a cyclic configuration, and (b) at least one saccharide selected from disaccharide, linear oligosaccharide and inulin, said enzyme decomposing said saccharide into monosaccharide, disaccharide, or both; and subsequently collecting the cyclic inulooligosaccharide from the thus obtained saccharide solution.

2. A method according to claim 1, wherein the saccharide solution containing cyclic inulooligosaccharide and at least one saccharide is obtained by a process in which an enzyme which acts on β-(2→1) bonded fructose polymer to produce cyclic oligosaccharide comprising 6–8 fructose molecules by way of an intramolecular transfer reaction or a microorganism which produces the enzyme is allowed to act on inulin.

3. A method according to claim 1, wherein the exo-enzyme having the ability to cut β-(2→1) fructoside bond is selected from the group consisting of β-fructofuranosidase, inulinase and inulobiose generating enzyme.

4. A method according to claim 1, further comprising contacting the saccharide solution after the exo-enzyme treatment with a gel filtration material.

5. A method according to claim 4, wherein the saccharide solution after the exo-enzyme treatment is subjected to chromatographic separation.

6. A method according to claim 5, wherein the chromatographic separation is performed by using a cation exchanger as a separating agent.

* * * * *